United States Patent
Fallin et al.

(10) Patent No.: US 9,446,224 B2
(45) Date of Patent: Sep. 20, 2016

(54) BARRIER CATHETER

(75) Inventors: Thomas Wade Fallin, Hyde Park, UT (US); Jean-Sebastien Merette, Chester Springs, PA (US); Patrick Michel White, West Chester, PA (US); Frank Phillips, Highland Park, IL (US); Kern Singh, Chicago, IL (US)

(73) Assignee: Vital 5, L.L.C., Logan, UT (US)

( * ) Notice: Subject to any disclaimer, the term of this patent is extended or adjusted under 35 U.S.C. 154(b) by 1202 days.

(21) Appl. No.: 13/240,708

(22) Filed: Sep. 22, 2011

(65) Prior Publication Data

US 2012/0071814 A1 Mar. 22, 2012

Related U.S. Application Data

(63) Continuation-in-part of application No. 12/667,870, filed on Feb. 10, 2011.

(60) Provisional application No. 61/385,309, filed on Sep. 22, 2010, provisional application No. 61/450,094, filed on Mar. 7, 2011, provisional application No. 61/494,810, filed on Jun. 8, 2011.

(51) Int. Cl.
*A61M 31/00* (2006.01)
*A61M 27/00* (2006.01)
*A61M 1/00* (2006.01)
*A61M 25/00* (2006.01)

(52) U.S. Cl.
CPC ............ *A61M 27/00* (2013.01); *A61M 1/008* (2013.01); *A61M 1/0084* (2013.01); *A61M 25/007* (2013.01); *A61M 2025/0073* (2013.01)

(58) Field of Classification Search
None
See application file for complete search history.

(56) References Cited

U.S. PATENT DOCUMENTS

| | | | |
|---|---|---|---|
| 3,572,340 A | 3/1971 | Lloyd et al. | |
| 3,823,720 A * | 7/1974 | Tribble | 604/43 |
| 3,854,477 A | 12/1974 | Smith | |
| 3,967,728 A | 7/1976 | Gordon et al. | |
| 4,048,996 A | 9/1977 | Mittleman et al. | |
| 4,364,394 A | 12/1982 | Wilkinson | |
| 4,445,897 A * | 5/1984 | Ekbladh et al. | 604/541 |
| 4,623,329 A | 11/1986 | Drobish | |
| 4,643,716 A | 2/1987 | Drach | |
| 4,692,153 A * | 9/1987 | Berlin et al. | 604/171 |
| D294,639 S | 3/1988 | Croll | |
| 4,786,500 A | 11/1988 | Wong | |

(Continued)

FOREIGN PATENT DOCUMENTS

| | | |
|---|---|---|
| JP | 09-108218 A | 4/1997 |
| JP | 11-319103 | 11/1999 |

(Continued)

OTHER PUBLICATIONS

International Search Report for International application No. PCT/US2011/052524, dated Apr. 27, 2012, 6 pages.

(Continued)

*Primary Examiner* — Jason Flick
*Assistant Examiner* — Eric Bryant
(74) *Attorney, Agent, or Firm* — Cary R. Reeves

(57) ABSTRACT

Devices and methods are provided to conduct fluid away from or deliver fluid to an area of a treatment site of a patient's body. In one example, a catheter includes a fluid exchange portion and a member attached to the fluid exchange portion for biasing fluid flow at the treatment site.

6 Claims, 4 Drawing Sheets

(56) References Cited

U.S. PATENT DOCUMENTS

| | | | |
|---|---|---|---|
| D300,947 S | 5/1989 | Utas-Sjoberg | |
| 4,925,452 A | 5/1990 | Melinyshyn et al. | |
| 5,034,006 A * | 7/1991 | Hosoda et al. | 604/317 |
| 5,100,395 A * | 3/1992 | Rosenberg | 604/284 |
| 5,120,304 A * | 6/1992 | Sasaki | 604/35 |
| 5,201,723 A | 4/1993 | Quinn | |
| 5,221,255 A | 6/1993 | Mahurkar et al. | |
| 5,234,406 A | 8/1993 | Drasner et al. | |
| 5,318,517 A | 6/1994 | Reiman | |
| 5,320,599 A | 6/1994 | Griep et al. | |
| 5,324,518 A | 6/1994 | Orth et al. | |
| 5,358,494 A | 10/1994 | Svedman | |
| 5,425,723 A | 6/1995 | Wang | |
| 5,433,713 A | 7/1995 | Trotta | |
| 5,458,582 A | 10/1995 | Nakao et al. | |
| 5,458,631 A | 10/1995 | Xavier | |
| 5,523,092 A | 6/1996 | Hanson et al. | |
| 5,533,986 A | 7/1996 | Mottola et al. | |
| 5,545,151 A | 8/1996 | O'Connor | |
| 5,549,603 A | 8/1996 | Feiring | |
| 5,616,121 A | 4/1997 | McKay et al. | |
| 5,647,859 A | 7/1997 | Lampropoulos et al. | |
| 5,647,860 A | 7/1997 | Roth et al. | |
| 5,665,076 A | 9/1997 | Roth et al. | |
| 5,681,274 A | 10/1997 | Perkins et al. | |
| 5,702,372 A | 12/1997 | Nelson | |
| 5,785,678 A | 7/1998 | Griep et al. | |
| 5,873,865 A | 2/1999 | Horzewski et al. | |
| 6,017,323 A | 1/2000 | Chee | |
| 6,117,125 A | 9/2000 | Rothbarth et al. | |
| 6,179,816 B1 | 1/2001 | Mottola et al. | |
| 6,193,704 B1 | 2/2001 | Winters | |
| 6,235,009 B1 * | 5/2001 | Skow | 604/317 |
| 6,325,788 B1 | 12/2001 | McKay | |
| 6,350,253 B1 | 2/2002 | Deniega et al. | |
| 6,514,517 B2 | 2/2003 | Jamiolkowski et al. | |
| 6,524,300 B2 | 2/2003 | Meglin | |
| 6,534,559 B1 | 3/2003 | Vanderlaan et al. | |
| 6,558,686 B1 | 5/2003 | Darouiche | |
| 6,569,839 B1 | 5/2003 | McKay | |
| 6,626,885 B2 | 9/2003 | Massengale | |
| 6,676,643 B2 | 1/2004 | Brushey | |
| 6,689,110 B2 | 2/2004 | Brushey | |
| 6,749,580 B2 | 6/2004 | Work et al. | |
| D499,017 S | 11/2004 | Nestenborg | |
| D499,643 S | 12/2004 | Nestenborg | |
| 6,878,128 B2 | 4/2005 | MacMahon et al. | |
| D505,067 S | 5/2005 | Nestenborg | |
| 6,893,414 B2 | 5/2005 | Goble et al. | |
| 6,921,541 B2 | 7/2005 | Chasin et al. | |
| 7,001,371 B1 | 2/2006 | McLaughlin et al. | |
| 7,004,923 B2 | 2/2006 | Deniega et al. | |
| 7,100,771 B2 | 9/2006 | Massengale et al. | |
| 7,119,062 B1 | 10/2006 | Alvis et al. | |
| 7,186,247 B2 | 3/2007 | Ujhelyi et al. | |
| 7,195,624 B2 * | 3/2007 | Lockwood et al. | 604/543 |
| 7,201,745 B2 | 4/2007 | DiMatteo et al. | |
| 7,232,425 B2 | 6/2007 | Sorenson et al. | |
| 7,282,214 B2 | 10/2007 | Willcox et al. | |
| 7,326,196 B2 | 2/2008 | Olsen et al. | |
| 7,438,711 B2 | 10/2008 | Deniega et al. | |
| 7,452,353 B2 | 11/2008 | Dal Porto et al. | |
| 7,462,165 B2 | 12/2008 | Ding et al. | |
| 7,462,177 B2 | 12/2008 | Brushey et al. | |
| 7,465,291 B2 | 12/2008 | Massengale | |
| 7,510,077 B2 | 3/2009 | Massengale et al. | |
| 7,510,550 B2 | 3/2009 | Deniega et al. | |
| 7,527,609 B2 | 5/2009 | Deniega et al. | |
| 7,534,224 B2 | 5/2009 | Triebes et al. | |
| 7,547,302 B2 | 6/2009 | Porto et al. | |
| 7,569,045 B2 | 8/2009 | Deniega et al. | |
| 7,575,593 B2 | 8/2009 | Rea et al. | |
| D605,757 S | 12/2009 | Sawyer | |
| D605,758 S | 12/2009 | Schwartz et al. | |
| 7,625,337 B2 | 12/2009 | Campbell et al. | |
| 7,699,830 B2 | 4/2010 | Martin | |
| 7,778,852 B2 | 8/2010 | Vasko et al. | |
| 7,780,638 B1 | 8/2010 | Deniega et al. | |
| 7,806,869 B2 | 10/2010 | Nilsson et al. | |
| 7,815,604 B2 | 10/2010 | Massengale et al. | |
| 7,828,790 B2 | 11/2010 | Griffin | |
| 7,854,730 B2 | 12/2010 | Dal Porto et al. | |
| 7,854,732 B2 | 12/2010 | Massengale et al. | |
| 7,942,864 B2 | 5/2011 | Hynes | |
| D640,787 S | 6/2011 | Chia et al. | |
| 7,959,623 B2 | 6/2011 | Massengale | |
| 8,157,759 B2 | 4/2012 | Castillejos | |
| 8,216,176 B2 | 7/2012 | Randolph | |
| 2002/0007204 A1 | 1/2002 | Goode | |
| 2002/0017296 A1 | 2/2002 | Hickle | |
| 2002/0082547 A1 | 6/2002 | Deniega et al. | |
| 2002/0177803 A1 | 11/2002 | Chappuis | |
| 2003/0009095 A1 | 1/2003 | Skarda | |
| 2003/0069541 A1 | 4/2003 | Gillis et al. | |
| 2003/0069551 A1 | 4/2003 | Bradley, III et al. | |
| 2003/0105511 A1 | 6/2003 | Welsh et al. | |
| 2003/0181864 A1 | 9/2003 | Deniega et al. | |
| 2004/0030281 A1 * | 2/2004 | Goble et al. | 604/28 |
| 2004/0054338 A1 | 3/2004 | Bybordi et al. | |
| 2004/0073194 A1 | 4/2004 | Olsen et al. | |
| 2004/0193262 A1 | 9/2004 | Shadduck | |
| 2005/0085769 A1 | 4/2005 | MacMahon et al. | |
| 2005/0177118 A1 | 8/2005 | Hoganson et al. | |
| 2005/0192638 A1 * | 9/2005 | Gelfand et al. | 607/3 |
| 2005/0272697 A1 | 12/2005 | Herzberg et al. | |
| 2006/0015089 A1 | 1/2006 | Meglin et al. | |
| 2006/0058731 A1 | 3/2006 | Burnett et al. | |
| 2006/0184098 A1 | 8/2006 | Barnitz | |
| 2006/0195059 A1 | 8/2006 | Freyman et al. | |
| 2006/0229573 A1 | 10/2006 | Lamborne | |
| 2006/0229586 A1 | 10/2006 | Farles | |
| 2007/0005004 A1 * | 1/2007 | Hynes | 604/43 |
| 2007/0010786 A1 | 1/2007 | Casey et al. | |
| 2007/0049909 A1 | 3/2007 | Esch et al. | |
| 2007/0073239 A1 | 3/2007 | Skansen et al. | |
| 2007/0106247 A1 | 5/2007 | Burnett et al. | |
| 2007/0118096 A1 | 5/2007 | Smith et al. | |
| 2007/0197959 A1 | 8/2007 | Panotopoulos | |
| 2007/0197970 A1 | 8/2007 | Shen-Gunther | |
| 2007/0219488 A1 | 9/2007 | Francescatti | |
| 2008/0033324 A1 | 2/2008 | Cornet et al. | |
| 2008/0045883 A1 | 2/2008 | Radojicic | |
| 2008/0119881 A1 | 5/2008 | Vetter et al. | |
| 2009/0182304 A1 | 7/2009 | Deniega et al. | |
| 2009/0184026 A1 | 7/2009 | Massengale et al. | |
| 2010/0000666 A1 | 1/2010 | Deniega et al. | |
| 2010/0222668 A1 | 9/2010 | Dalke et al. | |
| 2011/0137267 A1 * | 6/2011 | Phillips et al. | 604/290 |
| 2012/0330295 A1 | 12/2012 | Marwaring et al. | |

FOREIGN PATENT DOCUMENTS

| | | |
|---|---|---|
| JP | 08-538960 A | 11/2008 |
| WO | 80/01139 A1 | 6/1980 |
| WO | WO9208514 A1 | 5/1992 |
| WO | WO9517918 A1 | 7/1995 |
| WO | WO9630064 A1 | 10/1996 |
| WO | WO9640325 A1 | 12/1996 |
| WO | WO9734655 A1 | 9/1997 |
| WO | WO9818510 A1 | 5/1998 |
| WO | WO0015277 A2 | 3/2000 |
| WO | WO0105210 A2 | 1/2001 |
| WO | WO 01/32068 A2 | 5/2001 |
| WO | WO0170322 A1 | 9/2001 |
| WO | WO2004101052 A2 | 11/2004 |
| WO | WO2004101052 A3 | 6/2005 |
| WO | WO2005110521 A1 | 11/2005 |
| WO | 2006/114637 A2 | 11/2006 |
| WO | 2006/114638 A2 | 11/2006 |
| WO | WO2007070096 A1 | 6/2007 |
| WO | WO2007142688 A1 | 12/2007 |
| WO | WO2007143179 A2 | 12/2007 |

(56) References Cited

FOREIGN PATENT DOCUMENTS

| WO | WO2009009367 A2 | 1/2009 |
|----|-----------------|--------|
| WO | WO2009009367 A3 | 1/2009 |
| WO | WO 2012/040311 A2 | 3/2012 |

OTHER PUBLICATIONS

Prior, David V., "Localised Drug Delivery via Collagen-Based Biodegradable Matrices," The Drug Delivery Companies Report Autumn/Winter 2004, pp. 39-42.

Innocoll, Inc., "Files US and Irish Patent Applications for its CollaRx® Bupivacaine Implant for the Management of Post-operative Pain," Mar. 29, 2007 10:49:32 AM, from http://www.innocoll-inc.com/.

Supplementary European Search Report for European patent application No. 08781266.5, dated Jun. 16, 2011, 9 pages.

International Preliminary Report on Patentability, for International application No. PCT/US2008/068998, dated Jan. 12, 2010, 1 page.

International Search Report for International application No. PCT/US2008/068998, dated Feb. 25, 2009, 3 pages.

English Abstract of JP 11-319103, dated Nov. 24, 1999, 1 pp.

\* cited by examiner

BARRIER CATHETER

CROSS-REFERENCE TO RELATED APPLICATIONS

This application is a continuation-in-part of U.S. patent application Ser. No. 12/667,870, filed Jul. 2, 2008, herein incorporated by reference. This application claims the benefit of U.S. Provisional Application No. 61/385,309, filed Sep. 22, 2010; U.S. Provisional Application No. 61/450,094, filed Mar. 7, 2011; and U.S. Provisional Application No. 61/494,810, filed Jun. 8, 2011, each of which is herein incorporated by reference.

FIELD OF THE INVENTION

The invention relates to devices and methods for transporting fluid to or from a treatment site of a patient's body.

BACKGROUND

Many medical procedures benefit from transporting fluid to or from a treatment site of a patient's body. Devices for transporting fluid in a medical procedure are generally referred to as catheters. They may be used to provide drainage or administer treatment fluids. For example, catheters may be used to drain fluids from organs or from areas of abnormal fluid collection such as in a surgical wound following a surgical procedure. Catheters may also be used to deliver fluid to a treatment site to provide a vast range of therapies from cancer treatment to nutritional supplementation. A few exemplary therapies include stimulating tissue growth, administering antibiotics, flushing away impurities, killing or halting the reproduction of cancer cells, and relieving pain.

Catheters may be used in gravity driven arrangements such as with a collection container located below the treatment site or a medication container located above the treatment site. Likewise, catheters may be used in pressurized arrangements. For example, suction may be applied to a drainage catheter to draw fluids away from the treatment site. Suction devices may include elastomeric bulbs, spring actuated bellows, electromechanical vacuum pumps, and other known medical suction devices. Pressurized fluid may also be delivered through a catheter to the treatment site. For example, fluid infusion devices may include manual syringes, elastomeric infusion devices, spring loaded infusion devices, electromechanical infusion devices, and other known infusion devices.

Typical prior catheters are linear devices having one or more openings formed along a portion of their length through which fluid passes. They often perform poorly due to an inability to drain fluids from or deliver fluids to a sufficiently large area to encompass the entire treatment site. In addition, tissue folds and tissue apposition further affect the movement and collection of fluid making it difficult for prior catheters to adequately address the treatment site. Prior catheters also indiscriminately aspirate or infuse the tissue surrounding the catheter with no ability to target or exclude specific areas. Indiscriminate aspiration or infusion may not provide the desired treatment and it may cause undesired interactions or harm to tissues not intended to be targeted by, for example, suction or treatment fluid. For example, anesthetics are sometimes infused into a surgical wound to provide post-surgical pain relief to disrupted tissues. It is undesirable for motor nerve roots to be anesthetized during pain treatment.

SUMMARY

Aspects of the invention provide devices and methods to conduct fluid away from or deliver fluid to an area of a treatment site of a patient's body. Fluid delivered to a treatment site will be referred to as treatment fluid and may be any material delivered to the treatment site to obtain a desired effect. For example treatment fluid may be water, saline, antibiotics, antiviral agents, hormones, growth factors, anti-inflammatories, analgesics, anesthetics, and/or any other material useful in treating a patient. For example, anesthetics may include marcaine, rupivicaine, bupivacaine, and/or any other anesthetic or combinations thereof.

The devices and methods of the illustrative examples may be used in a variety of patient interventions. For example they may be used to deliver fluids to or remove fluids from a surgical site. For example they may be used to deliver medications to remove post-operative pain or drain fluids from a post-operative wound. Examples of such surgical procedures include surgery of the head, neck, chest, back, abdomen, and the extremities. Examples include general surgery, cosmetic surgery, joint surgery, and spine surgery. However, it will be apparent to one having skill in the art that the disclosed devices and methods may be used to treat a variety of other conditions by drainage of fluids from and delivery of fluids to a treatment site.

In one aspect of the invention, a catheter includes a first or connection end and an opposite, second or terminal end. A fluid conduit extends between the connection end and the terminal end for passing fluids. The terminal end includes a fluid exchange portion. The fluid exchange portion may include an elongated hollow body having a wall defining the terminal end of the fluid conduit and one or more openings formed through the wall for passage of fluid between the fluid conduit and an exterior of the conduit. The terminal end may include more than one conduit. Multiple conduits may be adjustable two-dimensionally and/or three-dimensionally relative to one another to vary the fluid distribution pattern of the terminal end. The multiple conduits may be mounted in a predetermined relative spaced relationship to one another.

The terminal end may include a member attached to the one or more conduits. The member may interconnect portions of the one or more conduits to position the portions in a desired configuration. The member may be flexible to allow repositioning of the portions from an original position to alternate positions.

The member may include a barrier to fluid flow to impede fluid flow in specific predetermined directions. The barrier may be connected to the one or more conduits to bias fluid flow in a preferential direction or to impede fluid flow in a non-preferential direction. The barrier may serve as a connecting member for spacing portions of the one or more conduits. The barrier may be permanently secured to the terminal end or removably secured to the terminal end. The barrier may be separate from the terminal end and placed relative to the terminal end to protect selected portions of the patient's anatomy from the fluid being delivered. The barrier may, for example, impede fluid flow by juxtaposition of a fluid impervious structure and/or by absorption of fluid. The barrier may be made resorbable or durable. The barrier may be made of polymers, ceramics, metals, plant tissue, animal tissue, and/or other suitable materials. The barrier may be in the form of a block, sheet, film, layer, sponge, and/or other suitable form adapted or adaptable to the anatomic site where the barrier function is desired. The barrier may be provided pre-shaped and sized for a particular application and/or it may permit intraoperative shaping and sizing by the user. For example, the barrier may be made of a thin polymer film. In another example, the barrier may be made of collagen forming a relatively fluid impervious membrane.

The barrier may separate tissue layers at the treatment site and maintain fluid communication between the tissue layers over a two-dimensional or three-dimensional treatment site to extend the effective treatment area. Furthermore, the barrier may extend peripherally into the tissue folds and irregularities to separate tissue layers and enhance fluid transport between the layers and adjacent the barrier. Enhancement of fluid transport reduces the number of catheters required to transport fluid to and/or away from the treatment site.

The one or more openings in the wall of the conduit may be positioned at any circumferential position around the wall. They may be placed parallel to the plane of the non-linear path of the terminal end so that they open within the space between tissue layers to avoid blocking of the openings by overlying tissue.

The barrier may have a predetermined shaped that conforms to the margins of a particular surgical site. The shape may be polygonal, ovoid, spiral, or random shaped.

The terminal end of the catheter may have a first configuration and a second configuration into which it may be modified. For example, the terminal end may have a deployed configuration for fluid transport to or from a treatment site and a delivery or removal configuration. The delivery or removal configuration may be smaller than the deployed configuration to ease placement or removal of the catheter at a desired location of a patient's anatomy. For example, the delivery or removal configuration may be folded, rolled, stretched, compressed, twisted, deflated, straightened and/or otherwise manipulated relative to the deployed configuration.

The catheter may be placed at the treatment site in an inside-out placement method in which it is placed in an open wound and the connection end is passed out of the patient's body leaving the terminal end at the treatment site. Alternatively, the catheter may be placed at the treatment site in an outside-in placement method in which the terminal end is introduced from outside the patient's body to the treatment site. Where a surgical incision is present near the treatment site, the catheter may extend through the incision. Alternatively, the catheter may extend through another opening, such as a stab incision, formed for the purpose of passing a portion of the catheter.

Conduits may be made of any suitable biocompatible material. For example, conduits may be made of a biocompatible polymer. For example, conduits may be made of a heat settable elastic polymer. For example, the conduit may be made of or contain a thermoplastic elastomer such as a styrenic block copolymer, polyolefin, thermoplastic polyurethane, thermoplastic copolyester, thermoplastic polyamide, and/or their various blends. For example, the conduit may contain or be made of a polyether block amide or PEBA. PEBA is available from Arkema under the trade name of PEBAX®.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1A:
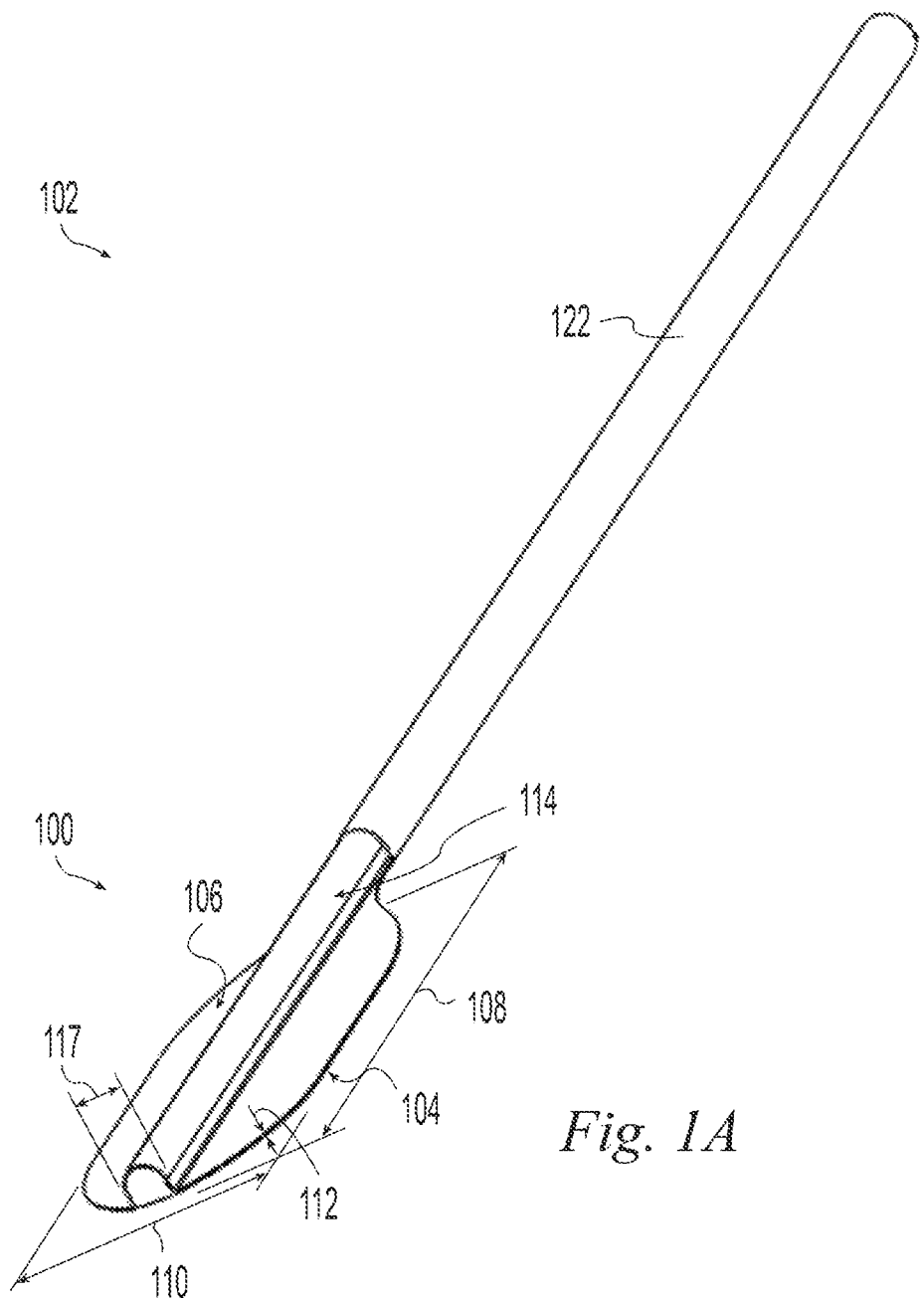
FIG. 1A is a bottom perspective view of an embodiment of the invention.

FIGS. 1A-1D depict a terminal end 100 of a catheter 102 having a front or "wet" side 104 and a back or barrier side 106. The terminal end 100 includes an elongated body 114 having a wall 116 defining an outer surface 118 and one or more elongated lumens. In the illustrative example of FIG. 1, the wall 116 defines a single, centrally positioned lumen 120 in fluid communication with a corresponding conduit 122 of the catheter 102. A plurality of wall openings 124 are spaced along the length of the elongated body 114 communicating from the lumen 120 to the outer surface 118 through the wall 116. The wall 116 has a width 117.

A barrier 126 is attached to the outer surface 118 of the elongated body 114 adjacent the openings 124. In the illustrative example of FIG. 1, the elongated body 114 is "D"-shaped with a flat side and the barrier 126 is attached to the flat side along the length of the elongated body 114 and is configured to lie in a plane with the elongated body 114 projecting outwardly from it. The barrier 126 has a length 108, a width 110, and a depth 112. The barrier 126 includes barrier holes 128 aligned with and in fluid communication with the wall openings 124 to allow fluid flow from adjacent the barrier surface into the lumen 120. The barrier 126 is fluid resistant and separates the front side 104 from the back side 106 of the terminal end 100. In the illustrative example of FIG. 1, the barrier is a fluid impermeable polyurethane membrane.

The terminal end 100 of FIG. 1 may be used to selectively direct treatment fluid to a treatment site. For example, the front side 104 may be positioned adjacent a treatment site and treatment fluid infused from lumen 120, through wall openings 124 and into contact with the treatment site. The barrier 126 blocks the flow of treatment fluid toward the back side 106 of the terminal end 100 to shield tissues adjacent the back side 106 from the treatment fluid.

In another example, the terminal end 100 of FIG. 1 may be used to selectively aspirate fluid from a treatment site. For example, the front side 104 may be positioned adjacent a treatment site and fluid aspirated through wall openings 124, into lumen 120 and out through conduit 122. The barrier 126 blocks the flow of fluid from the back side 106 of the terminal end 100 to shield tissues adjacent the back side 106 from the low pressure associated with aspiration.

Figure 1B:
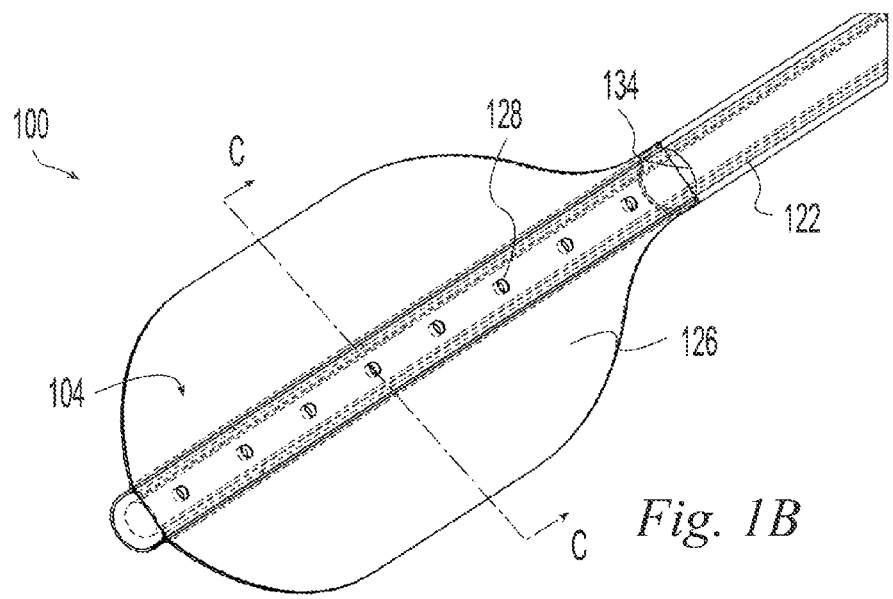
FIG. 1B is a top perspective view of the embodiment of FIG. 1A.
Figure 1C:
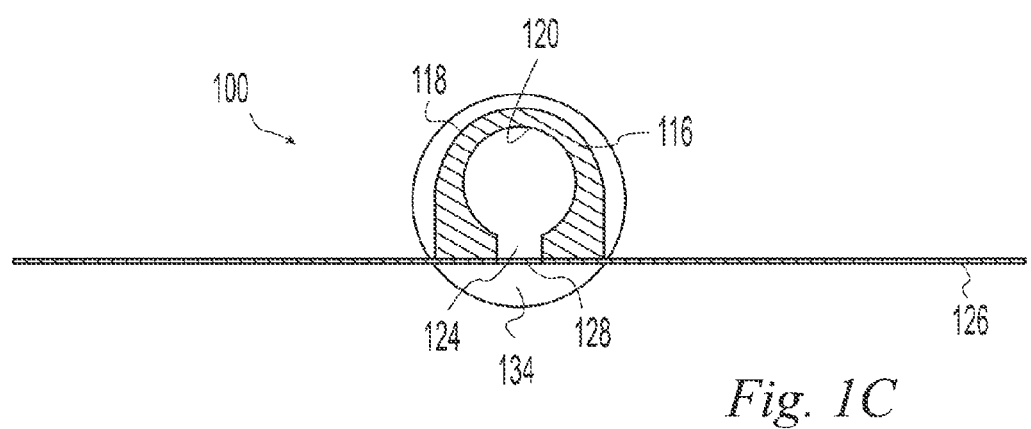
FIG. 1C is a cross-sectional view taken along line C-C of FIG. 1B.
Figure 1D:
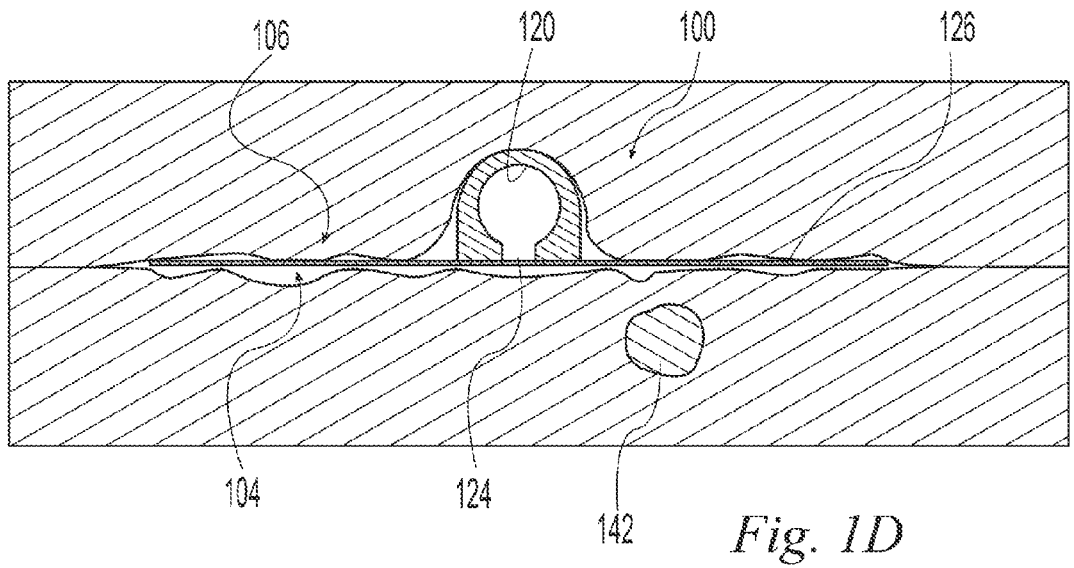
FIG. 1D is a cross-sectional view taken along line C-C of FIG. 1B and further illustrating the embodiment of FIG. 1A in place at a treatment site.

In the illustrative example of FIG. 1D, the terminal end 100 of FIG. 1 may be used as an aspiration catheter in combination with a separate source of treatment fluid (not shown). For example, the terminal end 100 may be positioned at a surgical site with the front side 104 adjacent to a nerve root 142 and the back side 106 toward a source of anesthetic fluid. As anesthetic fluid is infused into the site, the flow of the anesthetic toward the nerve root is impeded by the barrier 126 and any body fluids and excess anesthetic are removed from the vicinity of the nerve root 142 through the openings 124, into lumen 120 and out through conduit 122.

Figure 1E:
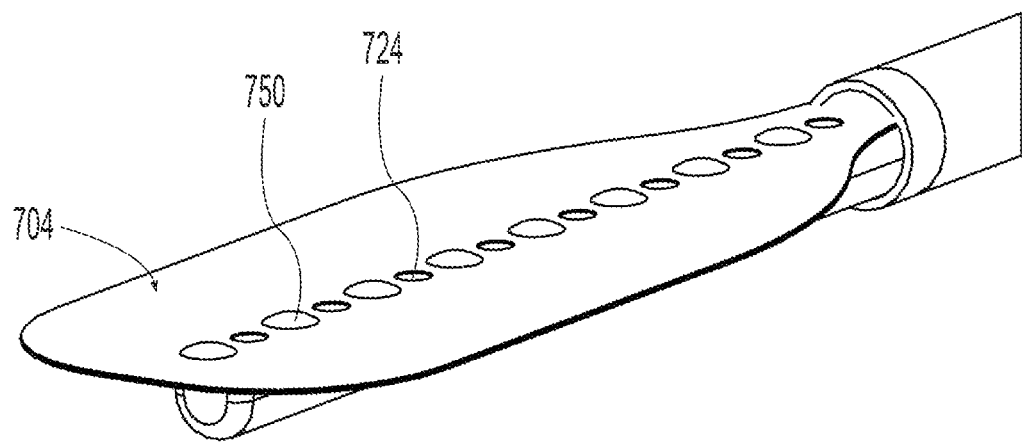
FIG. 1E is a perspective view of an embodiment of the invention similar to FIG. 1A illustrating an alternate surface texture.

In the illustrative example of FIG. 1E, a front side 704 further includes projections 750 creating a textured surface to improve fluid flow through openings 724. The projections prevent adjacent tissue from pressing against, or being drawn into, and sealing the openings 724. In the illustrative example, the projections are a plurality of bumps alternating with openings 724. However, the projections 750 may be distributed across the surface of the front side of elsewhere on the terminal end 100 to improve fluid flow. The projections may be molded integrally with the front side 704, adhered to the front side 704, formed by deforming the front side 704, deposited, cast, and/or otherwise formed. For example, the projections 750 may be formed by depositing a liquid compound and causing it to cure into a solid polymer such as a UV curable adhesive.

In the illustrative example of FIG. 1, the catheter 102 has a larger diameter than the elongated body 114 and defines a step 134 between them. This change in diameter facilitates removal of the terminal end 100 by withdrawal through an opening in the patient's body sized for the catheter 102. Pulling on the catheter 102 to extract the terminal end 100 from the treatment site tends to cause the terminal end 100 to collapse behind the step 134 for easier passage through a tissue opening.

In the illustrative example of FIG. 1, the barrier width 110 may be between 1 and 100 times the wall width 117. More particularly, the barrier width 110 may be between 2 and 20 times the wall width 117. More particularly, the barrier width may be between 2 and 5 times the wall width.

Figure 2A:
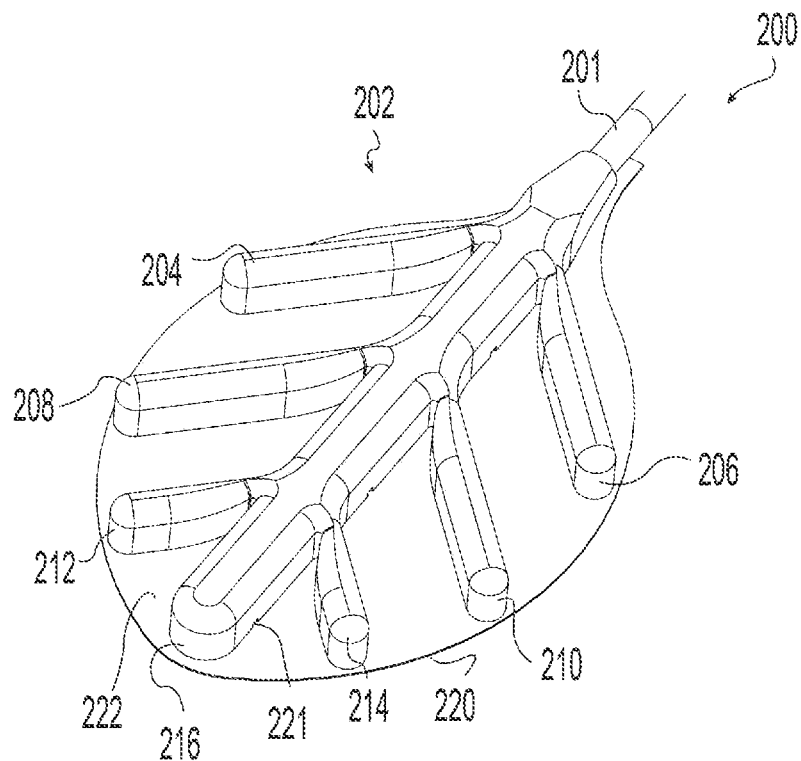
FIG. 2A is a top perspective view of an embodiment of the invention.
Figure 2B:
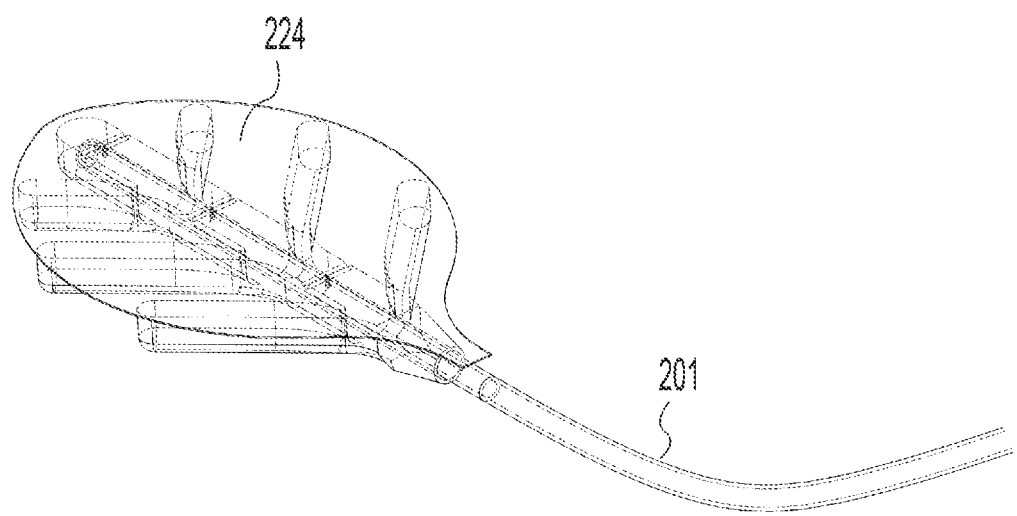
FIG. 2B is a bottom perspective view of the embodiment of FIG. 2A.

FIGS. 2A-B depict a terminal end 200 of a catheter 201 similar to that of FIGS. 1A-C. The terminal end 200 includes a palmate network 202 of conduits 204, 206, 208, 210, 212, 214, 216 including openings 221 for passing fluid between the interior of the conduits 204-216 and the exterior. In this example, peripheral conduits 204-214 extend in a generally divergent pattern from a central conduit 216 much like the vein pattern of a leaf. A member 220 having a first, front surface 222 and an opposing second, back surface 224 is attached to one side of the network 202, for example, to underlie the network. The conduits 204-216 tend to spring open into a deployed configuration and the member 220 interconnects the conduits 204-216 to maintain a desired spatial configuration. The member 220 may also form a barrier as in the example of FIG. 1. In an infusion arrangement, fluid exits the conduits 204-216 and is delivered to the first surface 222 and is distributed over the first surface to an area of the treatment site. In an aspiration arrangement, fluid collects on the surface 222 and is removed through openings 221 and conduits 204-216. The conduits 204-216 in this example are relatively thick polygonal structures that tend to separate adjacent tissue into folds at the treatment site to facilitate fluid communication over an area within the treatment site. The conduits 204-216 may be semi-rigid to facilitate tissue separation. Semi-rigid conduits also facilitate maintaining fluid flow by resisting crushing or kinking such as, for example, due to patient movement. The member 220 may be in the form of a thin sheet-like membrane. In the illustrative example of FIG. 2, the member is a fluid impermeable polyurethane membrane.

Each of the various examples of terminal ends described herein have a length, a width, and a depth. The length of the terminal end may vary over a broad range to suit a variety of treatment sites. For example, the length may range from a few millimeters to tens of centimeters. In particular, the length may range from 1 to 30 centimeters. More particularly the length may range from 5 to 20 centimeters. The width of the terminal end may vary over a broad range to suit a variety of treatment sites. For example, the width may range from a few millimeters to tens of centimeters. In particular, the width may range from 0.5 to 30 centimeters. More particularly the width may range from 1 to 15 centimeters. The depth of the terminal end may vary over a broad range to suit a variety of treatment sites. For example, the depth may range from a fractions of a millimeter to tens of millimeters. In particular, the depth may range from 0.05 to 20 millimeters. More particularly the depth may range from 0.5 to 10 millimeters.

A treatment kit may be provided including one or more infusion catheters according to various aspects of the invention. Optionally, the kit may include a protective barrier that may be integrated with or placed separately from the catheter to shield specific tissues. Optionally the kit may include an infusion pump.

In describing aspects of the invention, various examples have been described. It is to be understood that the features from one example may be incorporated into other examples.

What is claimed is:

1. A method of transporting fluid between a treatment site of a patient and a location outside of the patient, the method comprising:

providing a catheter having a connection end locatable outside of the patient, an elongated fluid conduit, and a terminal end locatable at the treatment site, the conduit defining a fluid path between the connection end and the terminal end, the terminal end comprising, a first fluid exchange portion having a wall defining an outer surface and an inner lumen in fluid communication with the elongated fluid conduit, the first fluid exchange portion having at least one opening communicating between the inner lumen and the outer surface of the wall, and a barrier connected to and extending from the first fluid exchange portion;

placing the terminal end from a location outside of the patient, through a tissue opening, to a location inside of the patient, at the treatment site;

positioning the barrier to bias fluid flow at the treatment site in a preferential direction or to impede fluid flow in a non-preferential direction; and extracting the terminal end through the tissue opening to transition the barrier from a deployed configuration to a collapsed configuration.

2. A method of delivering fluid to a treatment site of a patient, the method comprising:

providing a catheter having a connection end locatable outside of the patient, an elongated fluid conduit, and a terminal end locatable at the treatment site, the elongated fluid conduit defining a fluid path between the connection end and the terminal end, the terminal end comprising, a first fluid exchange portion having a wall defining an outer surface and an inner lumen in fluid communication with the elongated fluid conduit, the first fluid exchange portion having at least one opening communicating between the inner lumen and the outer surface of the wall, and a barrier connected to and extending from the first fluid exchange portion;

placing the terminal end from a location outside of the patient, through a tissue opening, to a location inside of the patient, at the treatment site with the at least one opening directed to deliver fluid to a target location;

positioning the barrier to shield non-target locations from the fluid; and extracting the terminal end through the tissue opening to transition the barrier from a deployed configuration to a collapsed configuration.

3. A method of removing fluid from a treatment site of a patient, the method comprising:

providing a catheter having a connection end locatable outside of the patient, an elongated fluid conduit, and a terminal end locatable at the treatment site, the elongated fluid conduit defining a fluid path between the connection end and the terminal end, the terminal end comprising, a first fluid exchange portion having a wall defining an outer surface and an inner lumen in fluid communication with the elongated fluid conduit, the first fluid exchange portion having at least one opening communicating between the inner lumen and the outer surface of the wall, and a barrier connected to and extending from the first fluid exchange portion;

placing the terminal end at the treatment site with the at least one opening directed to remove fluid from a target location;

positioning the barrier from a location outside of the patient, through a tissue opening, to a location inside of the patient, to shield non-target locations from fluid removal; and extracting the terminal end through the tissue opening to transition the barrier from a deployed configuration to a collapsed configuration.

4. A method of delivering anesthetic to body tissue adjacent a nerve and simultaneously draining body fluids at a treatment site of a patient, the method comprising:

providing a first anesthetic infusion catheter having a fluid delivery end;

providing a second drainage catheter having a terminal end, the terminal end comprising a fluid exchange portion having a wall defining an outer surface and an inner lumen, the fluid exchange portion having at least one opening communicating between the inner lumen and the outer surface of the wall, and a barrier connected to and extending from the fluid exchange portion;

placing the terminal end of the first anesthetic infusion catheter at the treatment site adjacent the body tissue;

placing the terminal end of the second drainage catheter from a location outside of the patient, through a tissue opening, to a location inside of the patient, at the treatment site with the at least one opening directed toward the nerve and the barrier between the body tissues undergoing treatment and the nerve;

delivering anesthetic to the body tissue via the first catheter;

impeding a flow of anesthetic toward the nerve with the barrier;

draining body fluid from the treatment site through the at least one opening; and extracting the terminal end through the tissue opening to transition the barrier from a deployed configuration to a collapsed configuration.

5. A method of removing fluid from a treatment site of a patient, the method comprising:

providing a catheter having a terminal end including a fluid exchange portion having an elongated tubular wall defining an outer surface and an inner lumen, the fluid exchange portion having at least one opening communicating between the inner lumen and the outer surface of the elongated tubular wall; and a planar member connected to the elongated tubular wall and extending outwardly on opposing sides of the elongated wall;

positioning the planar member from a location outside of the patient, through a tissue opening, to a location inside of the patient, between tissue layers at the treatment site;

conducting fluid from the treatment site along the surface of the member to the fluid exchange portion;

removing fluid from the treatment site through the fluid exchange portion; and extracting the terminal end through the tissue opening to transition the planar member from a deployed configuration to a collapsed configuration.

6. A method of delivering fluid to a treatment site of a patient, the method comprising:

providing a catheter having a terminal end including a fluid exchange portion having an elongated tubular wall defining an outer surface and an inner lumen, the fluid exchange portion having at least one opening communicating between the inner lumen and the outer surface of the elongated tubular wall, a planar member connected to the elongated tubular wall and extending outwardly on opposing sides of the elongated tubular wall;

positioning the planar member from a location outside of the patient, through a tissue opening, to a location inside of the patient, between tissue layers at the treatment site;

delivering fluid through the fluid exchange portion to the planar member;

dispersing the fluid at the treatment with the member; and extracting the terminal end through the tissue opening to transition the planar member from a deployed configuration to a collapsed configuration.

* * * * *